United States Patent
Kalayeh

(10) Patent No.: US 7,474,685 B2
(45) Date of Patent: Jan. 6, 2009

(54) MULTI-LINE TUNABLE LASER SYSTEM

(75) Inventor: Hooshmand M. Kalayeh, Pittsford, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 435 days.

(21) Appl. No.: 11/135,768

(22) Filed: May 24, 2005

(65) Prior Publication Data

US 2006/0268947 A1    Nov. 30, 2006

(51) Int. Cl.
*H01S 3/10* (2006.01)
*H01S 5/00* (2006.01)

(52) U.S. Cl. .................. 372/50.12; 372/20
(58) Field of Classification Search ............ 372/20, 372/50.12; 356/437
See application file for complete search history.

(56) References Cited

U.S. PATENT DOCUMENTS

| | | | |
|---|---|---|---|
| 4,001,764 A | 1/1977 | Holland et al. | |
| 4,450,356 A | 5/1984 | Murray et al. | |
| 4,489,239 A | 12/1984 | Grant et al. | |
| 4,871,916 A | 10/1989 | Scott | |
| 5,166,789 A | 11/1992 | Myrick | |
| 5,250,810 A * | 10/1993 | Geiger | 250/338.5 |
| 5,410,154 A | 4/1995 | Broicher et al. | |
| 5,481,476 A | 1/1996 | Windig | |
| 5,818,951 A | 10/1998 | Schivley | |
| 6,366,681 B1 * | 4/2002 | Hutchins | 382/110 |
| 6,509,566 B1 | 1/2003 | Wamsley et al. | |
| 6,674,522 B2 * | 1/2004 | Krantz et al. | 356/237.1 |
| 6,725,705 B1 | 4/2004 | Huebler et al. | |
| 6,822,742 B1 * | 11/2004 | Kalayeh et al. | 356/437 |
| 2003/0030001 A1 | 2/2003 | Cooper | |
| 2004/0011948 A1 * | 1/2004 | Tobiason | 250/231.13 |

FOREIGN PATENT DOCUMENTS

EP    0 489 546 A2    6/1992

OTHER PUBLICATIONS

Werner Zirnig et al., "Innovative Technologies Improve Environmental Protection—Detection of Gas Leaks by Helicopter-Borne Infrared Laser System" pp. 1-7.

(Continued)

*Primary Examiner*—Minsun Harvey
*Assistant Examiner*—Patrick Stafford
(74) *Attorney, Agent, or Firm*—Ratner Prestia

(57) ABSTRACT

A multi-line tunable laser system, which uses lasers as light sources to illuminate, identify and or quantify one or more targets based on multi-dimensional spectral characteristics of each target. The system includes a plurality of laser sources, each tunable to emit an electromagnetic wave, and at least one tuning controller for tuning and locking each beam of light to a wavelength of required spectral line-width. The system also includes a transmitter for transmitting each beam of light to illuminate one or more targets, and a receiver for receiving light returning from the targets and converting the returned light to electrical signals for identifying and or quantifying the targets. The system further includes N tunable lasers where, M of the N lasers are each tuned to a wavelength that is partially absorbed by the targets, and L of the N (one or more) of the lasers are each tuned to a wavelength that is absorption-free of the targets.

17 Claims, 9 Drawing Sheets

OTHER PUBLICATIONS

Egor V. Degtiarev et al., "Compact mid-infrared Dial lidar for ground-based and airborne pipeline monitoring", SPIE, vol. 4882, 2003, pp. 432-441.

S. Brunsgaard et al., "High-Pressure Measuring Cell for Raman Spectroscopic Studies of Natural Gas", Applied Spectroscopy, vol. 55, No. 1, 2001, pp. 55-60.

* cited by examiner

MULTI-LINE TUNABLE LASER SYSTEM

BACKGROUND OF THE INVENTION

Surveillance of ground topography is well known in the art. In ground surveillance, it is highly desirable to detect whether there has been a material failure in a man-made object such as a road, a pipeline, an electrical grid, or another man-made structure of practical interest. When a structural failure is detected, proper authorities make a determination whether remedial action is necessary. Often times a land-based crew conducts a visual inspection of the ground topography to determine if there is a material failure by traversing an area by vehicle or foot. It is frequently the case that an aircraft or a satellite includes an image capture device such as a charge coupled device (CCD), complementary metal oxide semiconductor device (CMOS) or a radiation detector, such as an infrared sensitive detector. It is well known that airborne photographic systems can also be used for capturing images of adjacent areas of the ground.

When electromagnetic radiation, interacts with matter several phenomena may occur, including scattering, absorption, transmission and reflection of the electromagnetic radiation. Spectral or spectroscopic analysis includes carefully examining, analyzing, and representing the interactions involving electromagnetic radiation and matter, in an orderly fashion, as a function of wavelength, frequency, or time. During spectroscopic analysis, different materials exhibit different scattering, absorption, reflection and transmission characteristics. These distinctive characteristics are determined by the chemical and physical structure of the materials. When a set of these distinctive characteristics are determined to a given level of certainty, as with the use of known test subjects, these spectroscopic results may be referred to as reference spectral signatures or reference spectra.

Natural gas, characteristically, contains a mixture of methane, ethane, and small amounts of other gases. Gas generated by the decomposition of organic matter, henceforth, referred to as swamp gas, only contains methane. It is highly desirable for any natural gas detection method to be able to distinguish between gases released as a result of a failure in a pipeline or a holding container versus emanating swamp gases, thus avoiding false alarms.

Oil pipelines contain significant concentrations of volatile dissolved gas compounds, including methane, ethane, and propane. Oil pipelines operate under pressure; leaks and a concomitant pressure drop result in escaping volatile components, and thereby provide a means for leak detection. Electromagnetic radiation may be directed onto an area containing gas and oil pipelines by a variety of means. Commonly, lasers are used, but other means, such as antennas for radio and microwave electromagnetic energy may be used. Hereafter, when electromagnetic radiation is directed onto a test subject area is referred to as an illuminant.

In detecting failures of gas and oil pipelines there is a particular problem, as the gas or oil pipeline is typically buried beneath ground level. In such cases, it is difficult to make a direct visual assessment of any failures in the pipeline. When failures do occur, they are manifest by the leakage of the pipeline contents, the leaking material produces a characteristic trace or signal. Typically, failures in pipelines are currently determined by having personnel walk the pipeline, on a periodic and costly basis, with some means to detect the trace emanating from the pipeline.

Gases can escape a pipeline and travel through subterranean earth to the earth's surface and then into the atmosphere. Consequently, the atmosphere can be monitored for gases that have escaped the pipeline. An association of gases detected in the atmosphere with a pipeline leak may be direct or indirect. An example of a direct association is the release of specific hydrocarbon gases to the atmosphere from subsurface oil and gas pipelines. Natural gas consists of 2 primary components, methane and ethane. The mixture ratio of methane and ethane may vary.

Measurement of both components and confirmation of the appropriate concentration ratio directly establishes the presence of a pipeline leak. In this case, association is direct in that the gas components themselves are emitted into the atmosphere, albeit with a potentially modified composition.

Methane is produced from thermal or biological breakdown of coal. The gas detected (methane) is not the same as the natural resource (coal), so the term "indirect" is used to describe this association. The term "indirect association" does not imply that the scientific basis for the association is weak. The process of converting coal to methane is well described in scientific literature.

U.S. Pat. No. 6,822,742, issued on Nov. 23, 2004 to Kalayeh et al., entitled SYSTEM AND METHOD FOR REMOTE QUANTITATIVE DETECTION OF FLUID LEAKS FROM A NATURAL GAS OR OIL PIPELINE, provides a system for remote quantitative detection of fluid leaks from a natural gas or oil pipeline by use of an airborne platform. The contents of the above referenced application are incorporated herein by reference in their entirety.

SUMMARY OF THE INVENTION

The present invention provides a multi-line tunable laser system for identifying multi-dimensional spectral characteristics of one or more targets. The system includes a plurality of laser sources, each tunable to emit a beam of light having a different electromagnetic wavelength, and at least one tuning controller for tuning and locking each beam of light to a respective predetermined wavelength of a narrow line-width. The system also includes a transmitter for transmitting each beam of light toward the targets, and a receiver for receiving light returning from the targets and converting the returned light to electrical signals for identifying the targets. The plurality of laser sources are each tunable to emit a beam of light in a different region of electromagnetic spectrum, for example, mid-infrared electromagnetic spectrum. For example, the system may be configured as a multi-line DIAL sensor having N ON-line and OFF-line lasers, wherein M of the ON-line lasers are each tuned to a wavelength that is partially or proportionally absorbed by the targets, and L of the OFF-line lasers are each tuned to a wavelength that is not absorbed by the targets (N=M+L). Furthermore, the multi-line tunable laser sensor may be configured for different uses. For example, the ON-line lasers or OFF-line lasers may each have the same or different wavelength, from a narrow band electromagnetic spectral region, or from different electromagnetic spectral regions.

The multi-line tunable laser system of the present invention includes N-lasers which are tuned to M different wavelengths for detecting one or more targets, where each target is characterized by M-spectral absorption lines, and L (one or more) lasers which are tuned to be minimally absorbed by the targets and maximally reflected by the background where each background is characterized by its L dimensional received reflection/backscattering characteristics.

The plurality of laser sources include Q-switches to repeatedly generate pulses of energy, in which the pulses of energy are arranged sequentially to form a burst of pulses, characterized by (a) each pulse having a predetermined pulse width, for example, between 10 nsec. and 100 nsec., approximately, (b) each pulse separated from each other pulse by a predetermined pulse-to-pulse interval, for example, between 100 nsec. and 150 nsec., approximately, and (c) each burst of pulses being repeated at a predetermined interval, for example, between 500 usec. and 1000 usec, approximately.

Another embodiment of the invention includes a multi-line differential absorption light detection and ranging (DIAL) system. The system includes multi-line DIAL laser sensors generating a plurality of continuously tunable laser output signals, a controller for tuning each of the multi-line DIAL laser sensors to generate a laser output signal at a predetermined wavelength, a transmitter for transmitting the predetermined wavelength output signals toward a target, a receiver for receiving backscattered light from the target or from the target-background (for example, ground surface cover types) and a plurality of detectors for detecting the backscattered light at each of the corresponding received wavelengths.

The multi-line DIAL laser sensors of the present invention generate (a) N ON-line and OFF-line laser output signals, the N ON-line laser output signals selected to identify M On-line characteristics of the target, and (b) L (one or more) OFF-line characteristics of the target-background, where each of the OFF-line laser output signals are selected to be absorption-free of the target.

The controller of the present invention includes a look-up-table (LUT) for selecting a predetermined multi-dimensional spectral characteristics of different targets (one or more targets). The ON-line and OFF-line laser output signals are tuned to predetermined wavelengths identified in the LUT.

Each multi-line DIAL laser sensor of the system may be pulsed to generate an output pulse of energy at a respective predetermined wavelength, and the controller may be configured to sequentially combine each output pulse of energy from each of the multi-line DIAL laser sensors and generate a burst of pulses for transmission to the targets. The burst of pulses may include N pulses for N multi-line DIAL laser sensors, in which N is the total ON-line and OFF-line laser output signals selected to identify N characteristics of the targets and background.

Another aspect of the invention includes a method for identifying and or quantifying one or more targets based on their multi-dimensional spectral characteristics of the one or more targets. The method includes the steps of: (a) emitting separate beams of light from a plurality of laser sources; (b) tuning and locking each beam of light emitted from the plurality of laser sources to a predetermined electromagnetic spectrum of a narrow line width; (c) transmitting each beam of light to illuminate the targets; (d) receiving light returning from the targets; and (e) converting the returned light to electrical signals for identifying and or quantifying the targets.

It is understood that the foregoing general description and the following detailed description are exemplary, but are not restrictive, of the invention.

BRIEF DESCRIPTION OF THE DRAWING

The invention is best understood from the following detailed description when read in connection with the accompanying drawing. Included in the drawing are the following figures.

DETAILED DESCRIPTION OF THE INVENTION

Figure 1:
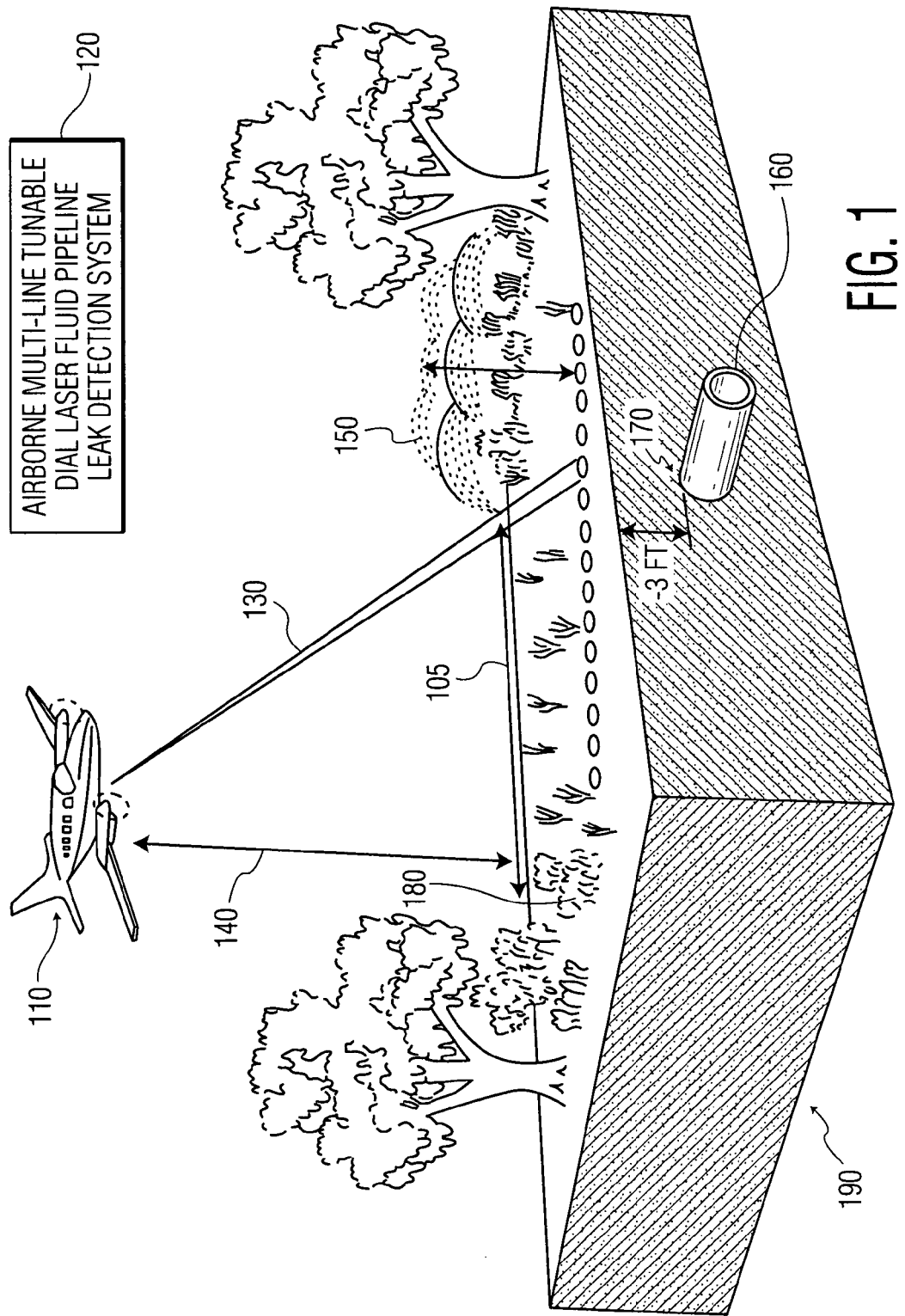
FIG. 1 is an exemplary schematic diagram of a multi-line tunable DIAL laser fluid pipeline leak detection system aboard an airborne platform, according to an embodiment of the present invention.

The present invention described herein addresses the measurement of target fluids, for example trace gases associated with oil and gas leakages from pipelines. This invention relates to an oil and gas pipeline leak detection system and method of detecting gases in the atmosphere and more particularly, but not by way of limitation, to detecting pipeline leaks based upon differential absorption lidar (DIAL) sensing techniques operating in a mid-infrared spectral range.

In general, many fluids may be detected or explored, such as gas, volatile oil, light crude oil, heavy crude oil, hazardous gases, hazardous liquids, or chemical and biological agents. Gas concentrations, for example, may be mapped over an area and the maps may be analyzed for concentration anomalies. These gas anomalies may be interpreted to determine underground pipeline leaks.

As used herein, the term "target fluids" indicates fluids that are either liquids or gases, for example, target fluids associated either directly or indirectly with pipeline leaks. The measured atmospheric concentrations of these target fluids form the basis of the present invention. Each target fluid has some unique characteristics in its association with the pipeline leak. For example, methane is produced in a number of ways. Methane may occur in the atmosphere as a result of emission from a hydrocarbon deposit, emission from a coal deposit, emission from wetlands with active populations of methane producing bacteria, emission from a leaking natural gas pipeline, etc.

Sources of methane other than a pipeline leak are said to be environmental interferences. Environmental interferences, which complicate the association between a target fluid and the pipeline leak, vary in magnitude and type according to factors such as soil type, hydrology, subsurface structure and composition, as well as atmospheric conditions, weather and land use.

The present invention may be configured to be used as a differential absorption lidar (DIAL) technique that samples a path through the atmosphere. A wide range of instruments have been developed which detect many trace gases in the atmosphere. There are many types of gas sources, which due to their spatial and temporal dynamics, cannot be accurately characterized by these techniques. Monitoring emissions from such sources requires a system that can remotely measure minute concentrations quickly and over long paths. Long path differential absorption lidars (DIALs) meet these requirements.

According to one aspect of the present invention, an airborne platform-based multi-line tunable differential absorption lidar (DIAL) laser optical system is used for remote quantitative detection of leaks from a natural gas or oil pipeline.

According to another aspect of the present invention, one or more targets, for example, the trace gases may be used to characterize fluid pipeline leaks based on a look-up table containing a listing of various gases and their respective multi-dimensional spectral characteristics. The multi-line tunable DIAL system, which includes N lasers (N=M+L), may be tuned to transmit M ON-line and L OFF-line predetermined wavelengths of energy. The N-wavelengths may be selected to detect one or more targets, for example, one or more gases, based on the DIAL multi-dimensional spectral characteristics as listed in the look-up table. In this manner, as contemplated by the inventor, the multi-line tunable DIAL system of the invention may be used in a variety of applications.

For example, when an aircraft is flying to detect one type of gas mixture, having a respective multi-dimensional spectral characteristics, the N lasers of the multi-line tunable DIAL system may be tuned to N different wavelengths, where N represents the number of spectral lines that characterizes the respective gas mixture (M ON-line wavelengths and L OFF-line wavelengths). Similarly, when an aircraft is flying to detect another type of gas mixture, having another respective multi-dimensional spectral characteristic, the N lasers of the system may be tuned to another set of N-wavelengths (M ON-line and L OFF-line) which characterizes that particular gas mixture.

It will also be appreciated that each of the ON-line and OFF-line lasers may be a tunable laser. As a tunable laser, an ON-line wavelength may be selected by tuning the respective laser to a specific wavelength. The tunable laser may be tuned in real time, by an operator disposed in a ground vehicle or flying aircraft. Depending on the mission, the operator may tune each laser to a predetermined wavelength to identify and quantify a specific characteristic of a target. The operator, for example, when notified that a specific target is desired to be identified and quantified, may use a look up table (LUT) that includes characteristics of different targets and a correspondence between these characteristics and laser ON-line or OFF-line wavelengths. The operator may then tune each laser, in real time, to these predetermined wavelengths. In addition, due to the real time capability of the DIAL system to be tuned to specific wavelengths, the operator may re-tune and re-lock each laser to another set of wavelengths, in real time. Operation may then continue, by searching for a different target having different characteristics.

According to another aspect of the present invention molecular transition of the optical absorption characteristics of multiple selected trace gases may be optimally selected from a look-up table. In order to simplify the discussion, only two trace gases are selected from the look-up table to exemplify the multi-line tunable DIAL laser system according to an embodiment of the present invention. In this example, the molecular transition of the optical absorption characteristics of methane and ethane within the mid-infrared region of the electromagnetic spectrum are selected. Therefore, a 3-line tunable DIAL laser system may be used to analyze and detect the two selected trace gases. Methane and ethane absorption characteristics may be analyzed with two ON-line wavelengths (also referred to as ON-line) and one OFF-line wavelength (also referred to as OFF-line) for the methane, ethane and the earth-surface type (background), respectively.

The ON-line wavelengths may be selected close to the peak of the target gas optical absorption with minimum interference from other gases. The OFF-line wavelength may be selected near the wing of the target gas optical absorption, with minimum interference from other gases and high ground surface reflectivity. The ON-line and OFF-line wavelengths may be selected to be 3369.8, 3389 and 3429 nanometers for ethane, methane and the background, respectively.

As previously described, tunable lasers may be used. Stable, continuously, tunable lasers may be designed to cover all trace gases and background in a look-up table. As described above, only two trace gases are selected to exemplify the multi-line tunable DIAL laser system according to the present invention. The inventor has determined that ND:YLF continuously tunable lasers may be used. For example, three ND:YLF continuously tunable lasers may be implemented for methane and ethane trace gases and background, respectively.

The present invention may also be used to measure concentration path-lengths of the target gases. Therefore, the multi-line tunable DIAL laser system, according to the present invention, may be used to measure the concentration path-lengths for selected target gases for each scanned spot. A 3-line tunable DIAL laser system, used to exemplify the current invention, measures the concentration path-lengths for the two selected target gases for each scanned spot shown in FIG. 1. The present invention may also employ an algorithmic or non algorithmic analysis of the multiple concentration path-length measurements for the two target gases along the flight path. Finally, the present invention may display, store and communicate the position, size and shape of the gas plumes associated with pipeline leaks.

The present invention, as schematically shown in FIG. 1, includes aircraft 110 (may also be groudborne, airborne, or spaceborne, such as a satellite, a helicopter or a ground based vehicle), an onboard multi-line tunable DIAL laser fluid pipeline leaks detection system 120, transmitted laser beam 130, trace gases 150, buried pipeline 160, leak area 170 and ground surface type 180. Also shown are a 3-dimensional section of the ground, including the pipeline, leak area and trace gases, generally designated as 190, an aircraft flight altitude 140, and an aircraft ground track 105. Based on a predetermined flight path, aircraft 110 flies along ground track 105. During the flight, an onboard GPS and inertial measurement unit (IMU) (not shown) guide the pilot along target location emanating trace gases 150. When the aircraft reaches the target location, laser beams 130 are automatically pointed to the target, as the scanner system scans the surrounding target region. The returned light is analyzed to develop gas-maps or images of the trace gas plumes in units of concentration path-length. In the example of FIG. 1, the returned light is analyzed to develop two-dimensional gas-maps or images of both methane and ethane plumes in units of concentration path-length.

In a 2-laser DIAL measurement system, in accordance with the invention, two single-wavelength, laser pulses are transmitted. One laser pulse of a specific wavelength is chosen which is absorbed by the gas of interest. The other laser pulse at a different wavelength is not absorbed. The energy reflected back to the sensor for both wavelengths is measured and combined to generate an estimate of the target gas concentration path length. This section describes this process in more detail.

The energy which is reflected back to the sensor is described by the following relationship:

$$E(\lambda_{on}, R) = \frac{E_t(\lambda_{on})\rho(\lambda_{on})\exp[-2(CPL + C_{bag} * R)\sigma(\lambda_{on})]}{R^2} \quad (1)$$

$$E(\lambda_{off}, R) = \frac{E_t(\lambda_{off})\rho(\lambda_{off})\exp[-2(CPL + C_{bag} * R)\sigma(\lambda_{off})]}{R^2} \quad (2)$$

where $E_t(\lambda_{on})$ and $E_t(\lambda_{off})$ is the ON-line and OFF-line transmitted laser pulse energy, $E(\lambda_{on},R)$ and $E(\lambda_{off},R)$ is the ON-line and OFF-line received laser pulse energy, $\rho(\lambda_{on})$ and $\rho(\lambda_{off})$ is the surface reflectance at ON-line and OFF-line wavelength respectively, CPL is the concentration path length of the plume, $C_{bag}$ is the background concentration of the target gas, R is the range or altitude, and $\sigma(\lambda_{on})$ and $\sigma(\lambda_{off})$ is the absorption cross-section of the target gas as a function of ON-line and OFF-line wavelength, respectively.

In the above, one may assume that $E_t(\lambda_{on})=E_t(\lambda_{off})$, $\rho(\lambda_{on})=\rho(\lambda_{off})$ and cross-sections $\sigma(\lambda_{on})$ and $\sigma(\lambda_{off})$ of the target gas at ON-line and OFF-line wave lengths do not change significantly due to pressure and temperature changes along the path. Otherwise, It may be necessary to re-measure $\sigma(\lambda_{on})$ and $\sigma(\lambda_{off})$.

By dividing the received measured ON-line laser pulse energy by OFF-line laser pulse energy, as shown in Equation 1 and 2, the following DIAL Equation may be derived:

$$\frac{E(\lambda_{on}, R)}{E(\lambda_{off}, R)} = \frac{\frac{E_t(\lambda_{on})\rho(\lambda_{on})\exp[-2(CPL + C_{bag} * R)\sigma(\lambda_{on})]}{R^2}}{\frac{E_t(\lambda_{on})\rho(\lambda_{on})\exp[-2(CPL + C_{bag} * R)\sigma(\lambda_{off})]}{R^2}} \quad (3)$$

Based on the above assumptions, equation (3) may be reduced to $$\frac{E(\lambda_{on}, R)}{E(\lambda_{off}, R)} = \frac{\exp[-2(CPL + C_{bag} * R)\sigma(\lambda_{on})]}{\exp[-2(CPL + C_{bag} * R)\sigma(\lambda_{off})]} \quad (4)$$

Where $E(\lambda_{on},R)$ denotes the laser energy measurement at ON-line wavelength, and $E(\lambda_{off},R)$ denotes the laser energy measurement at an OFF-line wavelength.

Taking the natural logarithm of equation (4), yields the following $$\frac{1}{2}\ln\left(\frac{E(\lambda_{on}, R)}{E(\lambda_{off}, R)}\right) = (CPL + C_{bag}R)(\sigma(\lambda_{off}) - \sigma(\lambda_{on})). \quad (4A)$$

The cross-section may be measured off-line or on-line (using one or more gas cells), as described later with respect to FIGS. 6 and 7. In either case, the cross-section at each wavelength becomes a known value. Therefore, Equation 4A may be rewritten as follows:

$$\frac{1}{2(\sigma(\lambda_{off}) - \sigma(\lambda_{on}))}\ln\left(\frac{E(\lambda_{on}, R)}{E(\lambda_{off}, R)}\right) = (CPL + C_{bag}R). \quad (5)$$

Equation 5 is the measurement process used in an embodiment of the invention having two single wavelength lasers. However, there may be additional processing possibilities, since R can also be measured by the system and $C_{bag}$ can be estimated or measured. It is then possible to produce an estimate of CPL:

$$CPL = \frac{1}{2(\sigma(\lambda_{on}) - \sigma(\lambda_{off}))}\ln\left(\frac{E(\lambda_{off}, R)}{E(\lambda_{on}, R)}\right) - C_{bag}R \quad (6)$$

In equation (6), the effect of differences in atmospheric absorption coefficient $\Delta C_a = 2(\int_0^R k_a(\lambda_{on},r) - k_a(\lambda_{off},r))dr)$ has not been considered. But equation (7) includes this effect, where $\Delta C_a$ can be estimated or measured.

$$CPL = \frac{1}{2(\sigma(\lambda_{on}) - \sigma(\lambda_{off}))}\left[\ln\left(\frac{E(\lambda_{off}, R)}{E(\lambda_{on}, R)}\right) - \Delta C_a\right] - C_{bag}R. \quad (7)$$

However, when the above assumptions do not hold true, it is likely that the above estimate of CPL may not accurately characterize the plume, and further analysis of the DIAL Equation (3) may be required.

The multi-line DIAL system is based on transmitting, receiving and measuring laser energies at multiple wavelengths through substantially the same optical path. For example, one laser wavelength, or the OFF-line wavelength, is selected so that the OFF-line laser energy is not absorbed by the presence of any constituent of interest. A second laser, or the ON-line wavelength is selected so that the laser energy is absorbed, as a function of a constituent target level of interest that is present in the path of the laser beam. By measuring the transmitted and received energy levels for a two laser line system, the following LIDAR equation (Equation 8 or 9) may be used to derive a more general DIAL equation (Equation 10) to determine a concentration path length measurement of any target constituent of interest, when system parameters, (for example, alignment, beam overlaps, beam and receiver field-of-view overlaps, ON-line and OFF-line geometric form factors, spectral response of receiver optics, and surface cover type reflectance) are not the same.

The LIDAR Equation may be, more generally, written in terms of ON-line and OFF-line transmitted and received laser energy or power, as follows:

$$E(\lambda, R) = E_t(\lambda)T_a(\lambda, R)T_p(\lambda, R)\xi(R)\rho(\lambda)\frac{D^2}{4R^2}T_a(\lambda, R)T_p(\lambda, R)\xi(\lambda) \quad (8)$$

Or $$P(\lambda, R) = P_t(\lambda)T_a(\lambda, R)T_p(\lambda, R)\xi(R)\rho(\lambda)\frac{D^2}{4R^2}T_a(\lambda, R)T_p(\lambda, R)\xi(\lambda) \quad (9)$$

where $E_t(\lambda)$ or $P_t(\lambda)$ is transmitted laser energy or power, respectively, $T_a(\lambda,R) = \exp(-\int_0^R k_a(\lambda,r)dr)$ denotes atmospheric transmission, $T_p(\lambda,R)=\exp(-\int_0^R k_p(\lambda,r)dr)$ denotes plume transmission,
$k_a(\lambda,r)$ is the atmospheric absorption coefficient,
$k_p(\lambda,r)$ is the plume absorption coefficient,
$\zeta(R)$ is the geometric form factor,
$\rho(\lambda)$ is the ground surface reflectivity, $$\frac{D^2}{4R^2}$$

is the solid angle of receiver optics,
R is the range/altitude of the sensor,
D is the telescope aperture,
$\zeta(\lambda)$ is the spectral response of the receiver, and
$E(\lambda,R)$ or $P(\lambda,R)$ is the scattered laser received energy or power respectively.

The DIAL Equation generally may be written, in terms of power or energy, as follows:

$$CPL = \frac{1}{2(\sigma(\lambda_{on})-\sigma(\lambda_{off}))}\left(\ln\left(\frac{P(\lambda_{off},R)P_t(\lambda_{on})\xi(R_{on})\xi(\lambda_{on})\rho(\lambda_{on})}{P(\lambda_{on},R)P_t(\lambda_{off})\xi(R_{off})\xi(\lambda_{off})\rho(\lambda_{off})}\right) - 2\left(\int_0^R k_a(\lambda_{on},r)-k_a(\lambda_{off},r)\right)dr\right)-R*C_{t-bag} \quad (10)$$

Or $$CPL = \frac{1}{2(\sigma(\lambda_{on})-\sigma(\lambda_{off}))}\left(\ln\left(\frac{E(\lambda_{off},R)E_t(\lambda_{on})\xi(R_{on})\xi(\lambda_{on})\rho(\lambda_{on})}{E(\lambda_{on},R)E_t(\lambda_{off})\xi(R_{off})\xi(\lambda_{off})\rho(\lambda_{off})}\right) - 2\left(\int_0^R k_a(\lambda_{on},r)-k_a(\lambda_{off},r)\right)dr\right)-R*C_{t-bag} \quad (11)$$

where
CPL is the concentration path length,
$\sigma(\lambda_{on})$ is the effective cross-section at $\lambda_{on}$ wavelength,
$\sigma(\lambda_{off})$ is the effective cross-section at $\lambda_{off}$ wavelength,
$P_t(\lambda_{on})$ is the transmitted laser pulse power,
$P_t(\lambda_{off})$ is the OFF-line transmitted laser pulse energy,
$E(\lambda_{on},R)$ is the ON-line received laser pulse energy,
$E(\lambda_{off},R)$ is the OFF-line received laser pulse energy,
$\zeta(R_{on})$ is the geometric form factor for the ON-line wavelength,
$\zeta(R_{off})$ is the geometric form factor for the OFF-line wavelength,
$\zeta(\lambda_{on})$ is the spectral response for the ON-line wavelength,
$\zeta(\lambda_{off})$ is the spectral response for the OFF-line wavelength,
$\rho(\lambda_{on})$ is the background surface reflectance for the ON-line wavelength,
$\rho(\lambda_{off})$ is the background surface reflectance for the OFF-line wavelength,
$k_a(\lambda_{on},r)$ is the atmospheric attenuation coefficient for the ON-line wavelength,
$k_a(\lambda_{off},r)$ is the atmospheric attenuation coefficient for the OFF-line wavelength,
R is the range/altitude/distance of the sensor to the target, and
$C_{t-bag}$ is the target gas/fluid concentration in the atmosphere.

In the above equations, only one trace gas is selected to exemplify the present invention. For two trace gases, a 3-line DIAL laser gas pipeline leak detection system may be used. For three trace gases, for example, a 4-line or more-line DIAL laser gas pipeline leak detection system may be used, etc.

A purpose for deriving the more general DIAL equation (Equation 11) is to point out that inaccurate wavelength selection, misalignment, different beam-spot-size, partially overlapping beams and surface reflectance variability lead to more complexity in quantitative detection of targets. Therefore, accuracy, stability and repeatability of the system parameters such as wavelengths, alignment, beam-spot sizes, beam-overlaps and accuracy in multi-dimensional characteristics of one or more targets provided by the present invention improves system simplicity, usefulness, robustness, sensitivity and performance capability.

In general, a multidimensional DIAL characteristic equation may be expressed as:

Case 1: the cross sections of other targets at the predetermined ON-line and OFF-line wavelengths for a selected target are zeros:

$$x_i = \frac{1}{2}\ln\frac{\frac{P(\lambda_{on\_line,i})}{P_t(\lambda_{on\_line,i})}}{\frac{P(\lambda_{on\_line,i})}{P_t(\lambda_{on\_line,i})}} = \cong (\sigma_{on,i}-\sigma_{off,i})CPL$$

Case 2: the cross sections of other targets at the predetermined ON-line and OFF-line wavelengths for a selected target are not zeros:

$$x_i = \frac{1}{2}\ln\frac{\frac{P(\lambda_{on\_line,i})}{P_t(\lambda_{on\_line,i})}}{\frac{P(\lambda_{on\_line,i})}{P_t(\lambda_{on\_line,i})}} = \cong \sum_{l=1}^{n}(\sigma^l_{on\_line,i}-\sigma^l_{off\_line,i})CPL_l$$

where i stands for the $i_{th}$ wavelength, l for the $l_{th}$ material and $CPL_l$ for concentration path length for material l, respectively. Then in an M dimensional space $$X = \begin{bmatrix} x_1 \\ x_2 \\ \ldots \\ \ldots \\ x_M \end{bmatrix} = \Sigma * CPL$$

$$\overline{X} = \begin{bmatrix} \overline{x_1} \\ \overline{x_2} \\ \ldots \\ \ldots \\ \overline{x_M} \end{bmatrix}$$

$$\text{Covariace}(X) = \frac{1}{Q}\sum_1^Q (X_j - \overline{X})(X_j - \overline{X})^T$$

The observed signals include multiplicative and additive noise, as follows:

$$Y=(\text{Multiplicative\_Noise})*X+\text{Additive\_Noise}$$

An optimal maximum likelihood estimate of CPL in multi-dimensional space is given by equation (12), as follows:

$$CPL=\{\Sigma^T[COV(X)]^{-1}\Sigma\}^{-1}\Sigma^T[COV(X)]^{-1}X \quad (12)$$

Figure 2A:
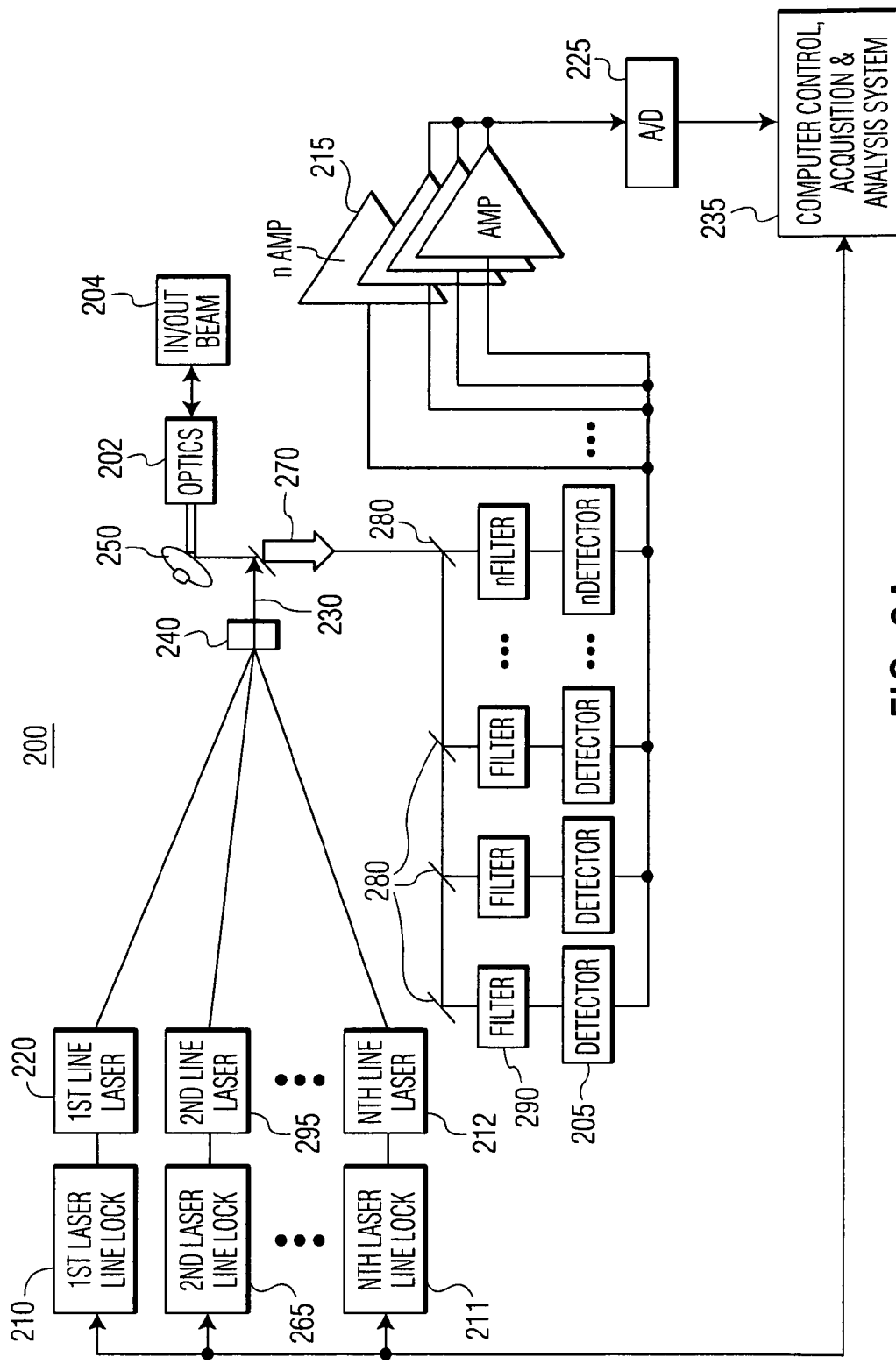
FIGS. 2A and 2B are block diagrams of multi-line tunable DIAL laser systems, according to an embodiment of the present invention.

Referring next to FIG. 2A, there is shown a multi-line tunable DIAL laser system, generally designated as 200. As shown, multi-line tunable DIAL laser system 200 includes N lasers of which M are ON-line lasers and L are OFF-line lasers (N=M+L).

For example, first line laser 220 may be an ON-line laser used for a first target trace gas, second line laser 295 may be a second ON-line laser used for a second target trace gas, etc. In one embodiment, the $N^{th}$ line laser 212 may be an OFF-line laser used for identifying a target-background. Other combinations of ON-line lasers and OFF-line lasers may be used in the N line lasers shown in FIG. 2. The N line lasers may be, respectively, locked onto N different wavelengths by line lock amplifiers 210, 265, etc., and 211.

More than one OFF-line lasers may be used for removing different variability of system parameters. For example, surface covered type (background) reflectance variability may be removed to obtain a more simple and reliable multi-line DIAL equation.

It is contemplated within the scope of the present invention that, in addition to lasers, other types of optical sources may be used. Furthermore, the ON-line wavelengths may be selected to be close to the peak of a target gas optical absorption characteristics and the OFF-line wavelengths may be selected to be near a wing of a target gas optical absorption wavelength.

The multiple ON-line and OFF-line laser beams are, respectively, combined by combiner 240 to form combined laser beam 230. The combined laser beam is reflected by mirror 250 into optics 202 to form output laser beam 204.

For the region of interest, trace gases in the atmosphere, near the ground, may be sequentially scanned by optics 202. Output laser beam 204 is scattered, transmitted through, and/or reflected back to form return light 270. Return light 270 passes through a set of beam splitters 280 prior to encountering a set of filters 290. These set of filters are tuned, respectively, to pass each of the multiple ON-line and OFF-line wavelengths. A set of detectors 205 convert each of the filtered lights into a respective electronic signal. The electronic signals are amplified by amplifiers 215 and then converted into digital signals by a set of analog-to-digital (A/D) converters 225. The digitized signals are processed and analyzed by computer 235 to identify and quantitatively measure one or more targets. These targets are detected based on the operator selected spectral absorption characteristics and based on the operator selected spectral non-absorption characteristics of the target-backgrounds.

Figure 2B:
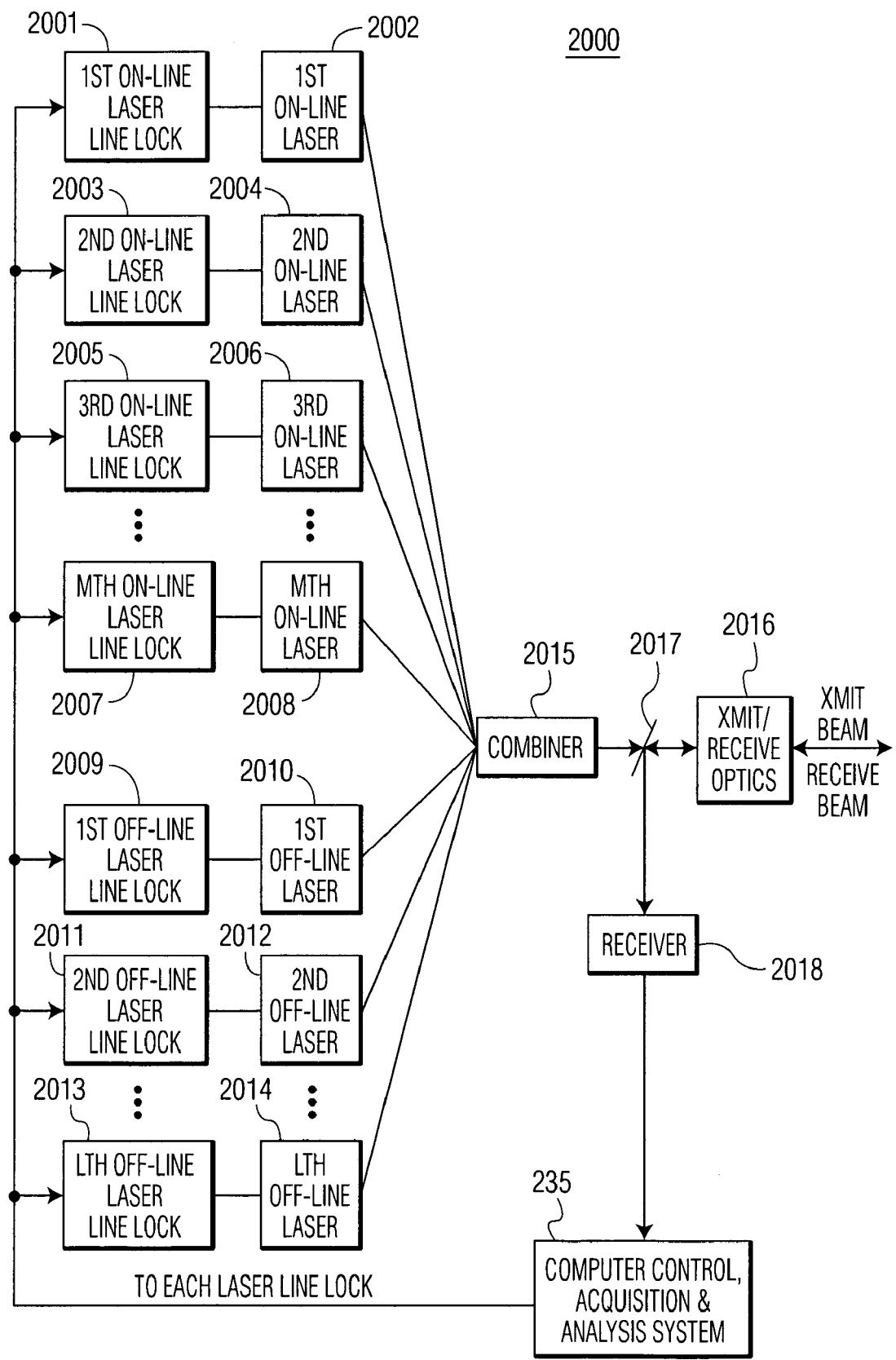

Referring next to FIG. 2B, there is shown a multi-line DIAL tunable laser system, generally designated as 2000. As shown, M ON-line laser outputs and L OFF-line laser outputs are provided by the system. The M ON-line lasers include first ON-line laser 2002, second ON-line laser 2004, third ON-laser 2006, etc., and $N^{th}$ ON-line laser 2008. The M ON-line lasers are locked onto M different wavelengths by first ON-line laser line lock 2001, second ON-line laser line lock 2003, third ON-line laser line lock 2005, etc., and $M^{th}$ ON-line laser line lock 2007, respectively.

System 2000 also includes L OFF-line lasers. As shown, system 2000 includes first OFF-line laser 2010, second OFF-line laser 2012, etc., and $L^{th}$ OFF-line laser 2014. Each of the L OFF-line lasers are locked onto L different wavelengths by first OFF-line laser line lock 2009, second OFF-line laser line lock 2011, etc., and $L^{th}$ OFF-line laser line lock 2013, respectively. As described with respect to FIG. 2A, the combination of M ON-line lasers and L OFF-line lasers add up to a total of N line lasers incorporated into system 2000.

The M ON-line lasers and the L OFF-line lasers provide output beams that are combined by combiner 2015 to produce a combined beam output. The combined beam output is provided by way of splitter 2017 to transmit/receive optics 2016, which in turn, provides the output transmitted beam to the targets. In a similar manner, a received beam is received by transmit/receive optics 2016 and provided to receiver 2017 by way of splitter 2017.

Figure 3:
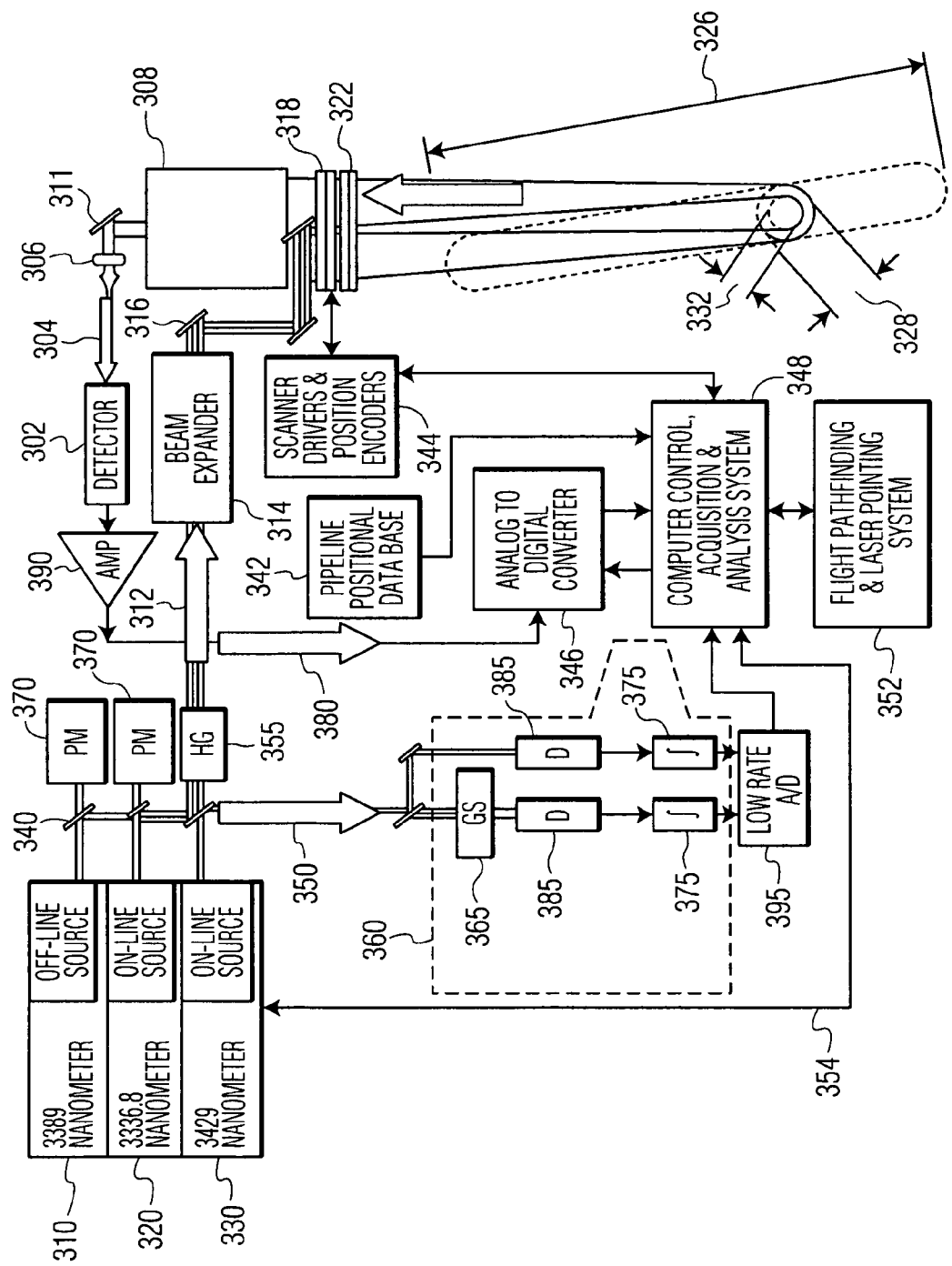
FIG. 3 is a block diagram of an exemplary embodiment of the multi-line tunable DIAL laser fluid pipeline leak detection system, according to an embodiment of the present invention.

A block diagram of a 3-line DIAL laser gas pipeline leak detection system to exemplify a multi-line laser system, is shown in FIG. 3. As shown, three laser sources for the OFF-line and two ON-line wavelengths, designated as 310, 320 and 330, respectively are split by three beam splitters 340 toward power meters 370, holographic grating 355 and gas cell subsystem 360.

Collinear beams 312, formed by holographic grating 355, enter into spatial fitter and beam expander 314 to provide a collimated expanded beam as a fixed finite source. Any drifts that may occur in laser alignment easily show up as transmitted pulse energy discrepancies, and do not affect gas concentration length measurements. The multi-wavelength source beam is then re-directed by optical path mirrors 316, and a galvanometer-driven scanning fast mirror 318. The beam is finally transmitted to illuminate the ground via a large aperture, slow scanning mirror 322, that is also used to compensate the scan swatch for aircraft roll and pitch errors.

As the galvanometer-driven scanning fast mirror 318 swings through a full angle of 25 degrees, for example, the source beam swings through a 50 degree arc on entering telescope 308. Telescope 308 produces a 5 degree full angle scan of the transmitted beam, and traces a 35 m wide ground swath, designated as 326, based on laser footprint 332 (the additional angle width is included to compensate for aircraft crab angle). Light scattered from receiver footprint 328, returns and enters the full telescope aperture via a slow track correction mirror. The fast scanning galvanometer-driven mirror 318 also reflects the received light in the exit pupil. Thus, the galvanometer-driven scanning fast mirror 318 shifts the field of view (FOV) of the receiver (equivalent to shifting receiver footprint 328 on the ground) synchronously with the optical centerline of the transmitted beam.

The received light passes through beam-splitter 311 and through narrow band interference filter 306. The filtered light 304 is then detected by detector 302 and amplified by amplifier 390. The amplified signal 380 is digitized by A/D converter 346.

In order to monitor the stability of the locked three wavelengths, a portion of the beam energy from ON-line laser sources 320 and 330 is bypassed to gas cell subsystem 360 as beam 350. The gas-cell 365 only passes selected laser lines, and the two detectors 385 convert the laser light to analog signals before passing these signals through two integrators (energy meters) 375 to be able to compare the energy transmitted through the known gas cell 365 with the energy bypassing the known gas cell 365. The integrated laser energies, as two analog signals, are digitized by low rate A/D converters 395 and output to computer control acquisition and analysis system 348.

Completing the description of FIG. 3, scanner controller 344 controls the fast scan mirror 318 and the slow scan mirror 322. Pipeline positional database 342 and flight path-finding and laser pointing subsystem 352 provide pipeline positional data and flight path data to computer control, acquisition and analysis system 348. The received signal, after detection and amplification, is sent to A/D converter 1146, by way of signal line 1180. After being digitized, the received signal is sent to computer control, acquisition and analysis system 1148. As also shown, system 1148 may select, tune and adjust the wavelengths of each of lasers 1110, 1120 and 1130.

Because the system of the invention may reside in a moving airborne platform, the multiple laser pulses ideally should be transmitted at the same time, so that all the pulses impinge the same optical spot. The inventor has determined, however, that the multi-laser pulses, for example, three laser pulses used to exemplify the 3 line laser system in FIG. 3, may be of pulse widths of about 20 nanoseconds each and time spacing between pulses of about 100 nanoseconds. These three pulses may be combined, as described later, into a single optical train as a pulse triplet set.

Figure 4:
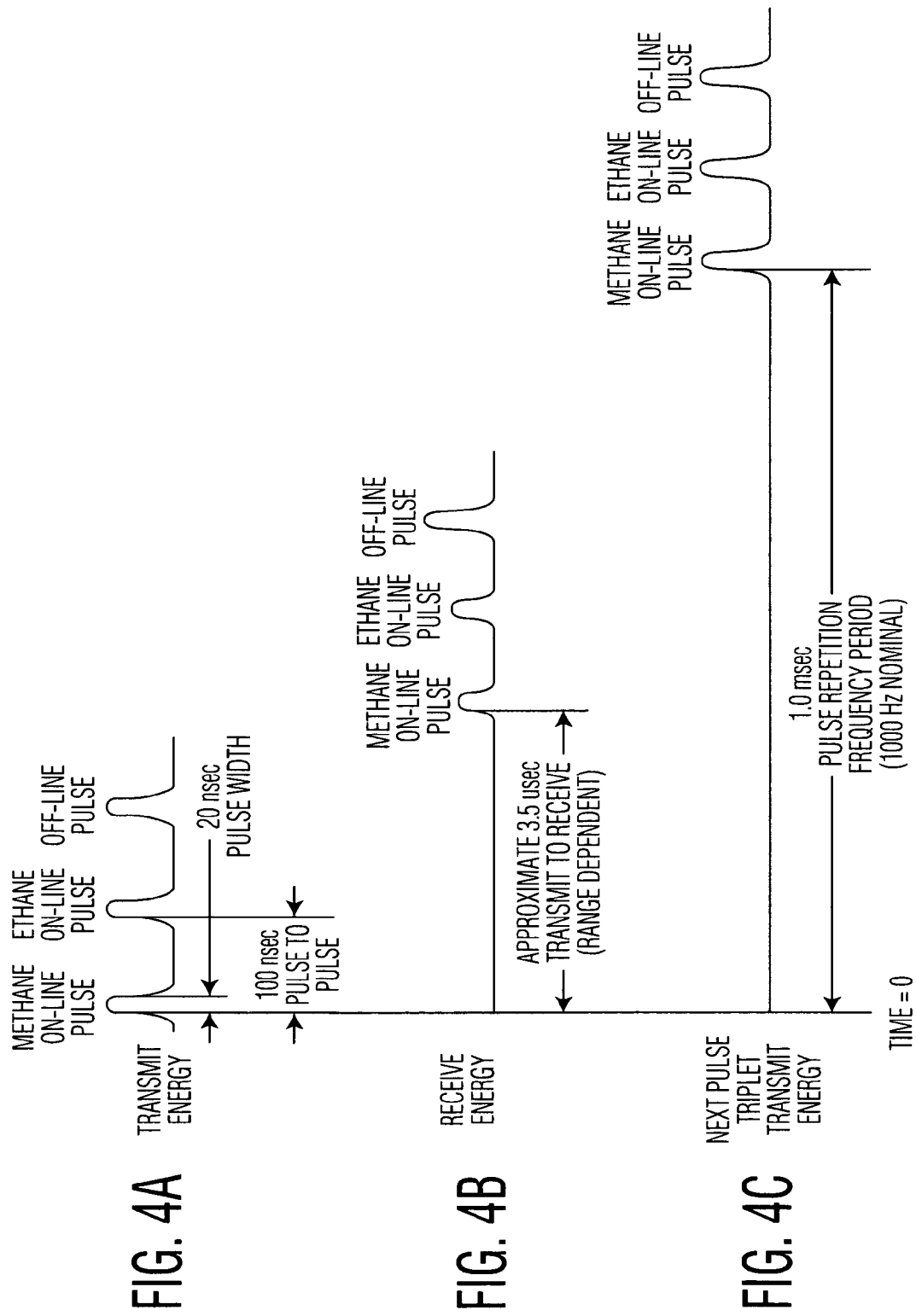
FIG. 4A-4C are timing diagrams of an exemplary pulse triplet set transmitted and received by the system of FIG. 3, according to an embodiment of the present invention.

FIGS. 4A, 4B and 4C show a timing diagram of an exemplary 3-line laser system that transmits the pulse triplet set according to the present invention. As shown in FIG. 4A, a single pulse triplet set, includes a methane ON-line pulse, an ethane ON-line pulse and an OFF-line pulse which are transmitted to the ground. Each pulse has a width of about 20 nsec and a time spacing between pulses of about 100 nsec. As shown in FIG. 4B, for a transmit and receive range of about 500 meters, about 3.5 microseconds elapses between the time the pulse triplet set is transmitted and the time the pulse triplet set is received. The smaller amplitudes of the received methane and ethane pulses illustrate energy being absorbed by absorption characteristics of the two trace gases. As shown in FIG. 4C, an exemplary pulse repetition interval may be 1.0 msec, and the pulse repetition frequency (PRF) may be 1000 Hz.

Figure 5:
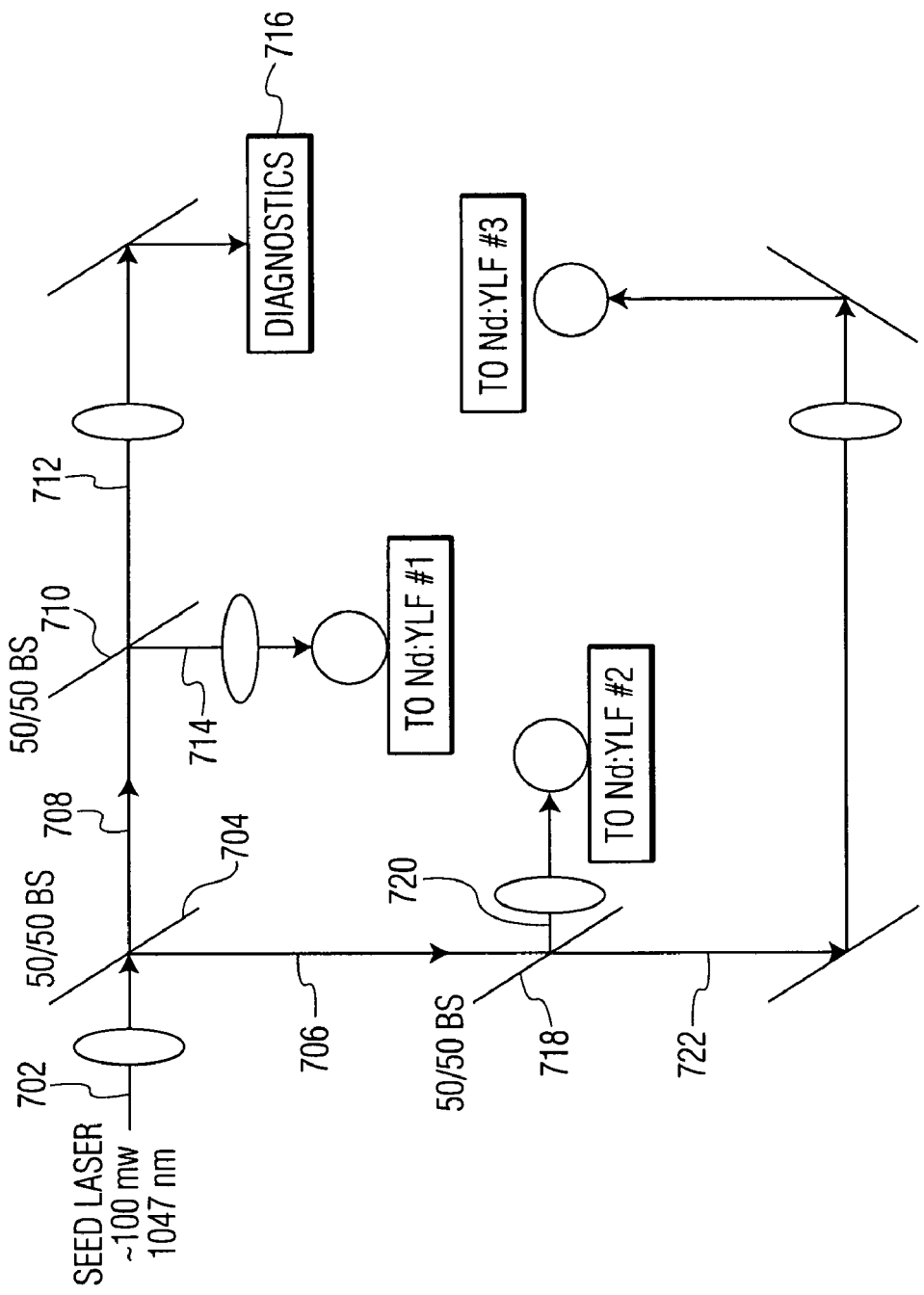
FIG. 5 is a schematic diagram of an exemplary distribution of a laser beam from a seed laser to three separate transmitter modules, according to an embodiment of the present invention.

FIG. 5 is a diagram of an exemplary distribution of a laser beam formed by a meteor seed laser. Meteor seed laser beam 702 is split in half by beam splitter 704 producing laser beams 706 and 708. Laser beam 708 is split in half by beam splitter 710 producing laser beams 712 and 714. Laser beam 712 is sent to diagnostics 716 and laser beam 714 is sent to a first of N transmitter modules. Laser beam 706 is split by beam splitter 718 producing laser beam 720 and laser beam 722. Laser beam 720 is sent to a second of N transmitter modules. Laser beam 722 is sent to a third of N transmitter modules. The interaction between the meteor seed laser and another two lasers to form a single source for transmission (for example one transmission out of N transmissions) is described by reference to FIG. 6.

Figure 6:
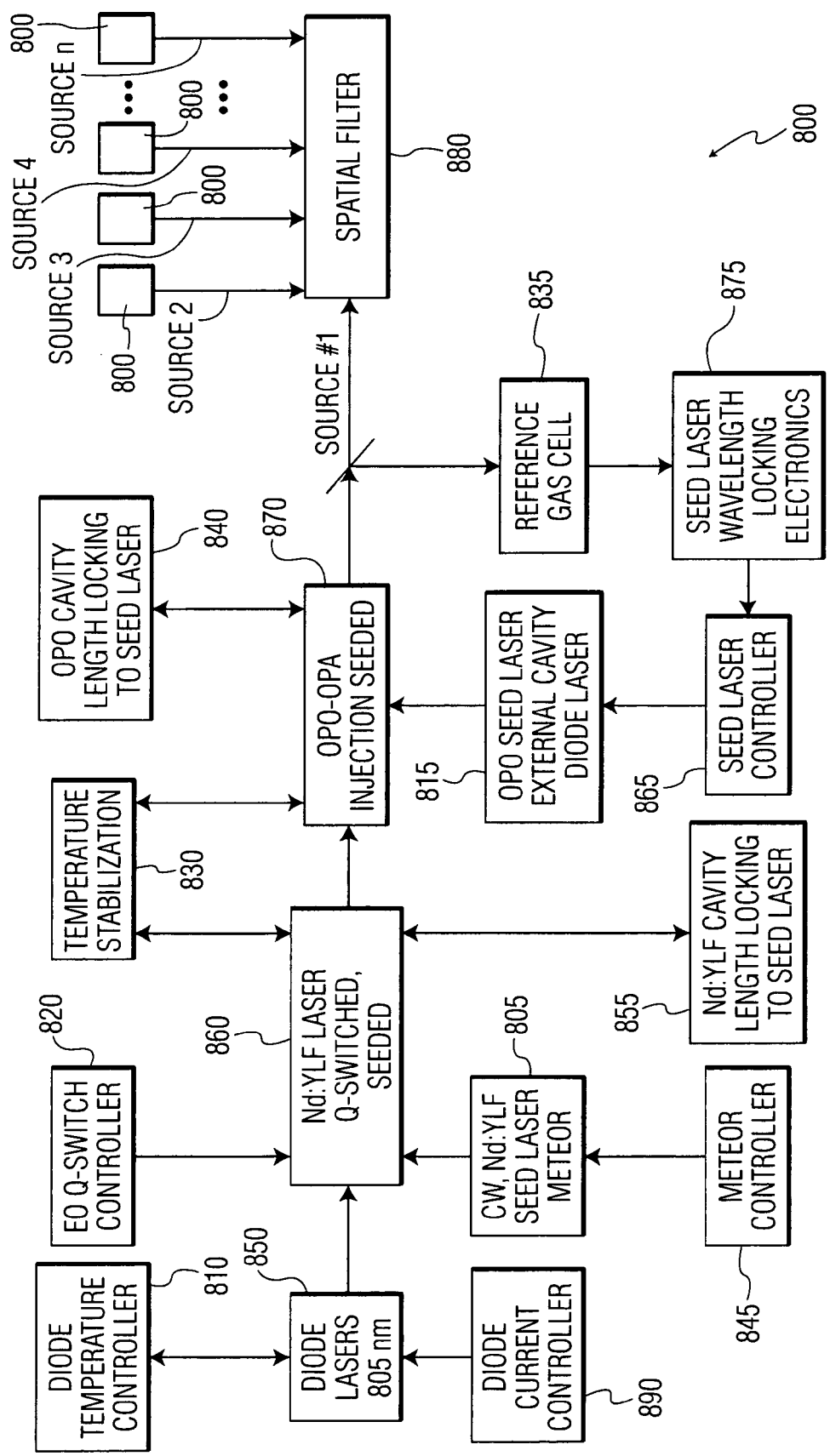
FIG. 6 is a block diagram illustrating use of three different lasers to form a final laser beam, denoted as source #1, according to an embodiment of the present invention.

FIG. 6 is a block diagram of an exemplary embodiment illustrating the use of three lasers to produce a final laser beam (source #1) according to an embodiment of the present invention. FIG. 6 shows N-transmitter modules, each designated as 800. For ease of explanation, one transmitter module 800 is shown in detail. As shown, meteor controller 845 controls meteor seed laser 805 to inject a 1047 nm seed laser into a laser cavity. The laser cavity length is locked by a voltage controlled oscillator (not shown) to maintain control over the 1047 nm meteor seed laser wavelength. This continuous wave (CW) laser is then optically locked (optical lock #1) by a PZT (piezo-electric transducer) on which an output coupler is mounted. The optical lock #1 is maintained using a dither-and-lock technique that dithers the PZT at >10 kHz and uses a resonance detector signal to derive a PZT correction signal.

Diode current controller 890 and diode temperature controller 810 control the output of Diode pump laser 850 at 805 nm. Output of the 805 nm pump diode laser (850) is collimated and focused into a Nd:YLF rod 860 to provide gain for the laser. EO Q-switch controller 820 and temperature stabilizer 830 operate to Q-switch the Nd:YLF rod with a KDP (potassium deuterium phosphate) Pockels cell to produce a 1047 nm pulsed laser output. The Nd:YLF rod is pumped for approximately 300 to 400 microseconds before turning the 805 nm pump off and then firing the Q-switch. A quarter-wave plate (not shown) is adjusted to provide just enough loss to hold-off the laser, i.e. prevent lasing, until the Q-switch is turned on. The total cavity length (HR to OC distance) is approximately 20 to 25 cm.

The 1047 nm Nd:YLF pulsed laser from rod 860 is then optically transmitted into an Optical Parametric Oscillator-Optical Parametric Amplifier (OPO-OPA 870). The OPO-OPA is a 4-mirror ring cavity containing 2 PPLN (periodically-poled lithium niobate) crystals. The first crystal (OPO) is chosen to produce approximately 3400 nm and approximately 1510 nm of light from the 1047 nm pump, while the second crystal (OPA) is chosen to produce approximately 3400 nm and approximately 2700 nm light with the approximately 1510 nm pump. The cavity resonates the approximately 1510 nm and is injection seeded at this wavelength through an output coupler. The cavity length is locked (optical lock #2) to the seed frequency by using a Pound-Drever-Hall (PDH) technique with RF (radio frequency) modulation applied to the diode laser of the approximate 1510 nm seed. One of four cavity mirrors is mounted on a PZT to allow fine cavity length adjustment. The total cavity length is approximately 8 cm.

As a result, each of the transmitter modules 800 produce a 20 nanosecond 3400 nm laser pulse approximately, which is filtered by spatial filter 880. Through timing control provided by computer 235 (FIG. 2A) and optical combining by the beam combiner shown in FIG. 7, a pulse from each of transmitter modules 800 are combined into an N-pulse set (a triplet set in FIG. 4A). The pulse sets may be generated at a PRF rate ranging from about 1000 Hz to about 2000 Hz.

The approximate 3400 nm wavelengths of the three output pulses of the system are critically important. To maintain the wavelengths, a portion of the transmit laser energy is bled off the main laser path through and around a reference gas cell (835 for example) onto two MWIR detectors. These detectors are then used by a dither-and-lock technique (optical lock #3) to lock the pulsed OPO-OPA output to the gas absorption feature (by way of modules 875, 865 and 815 in FIG. 6).

Transmitter module #1 may produce a 3429.0 nm laser pulse, transmitter module #2 may produce a 3389.0 nm laser pulse and transmitter #3 may produce a 3336.8 nm laser pulse for the ON-line (methane), OFF-line and ON-line (ethane) wavelengths, respectively.

After the three laser pulses are produced by the exemplary 3-line embodiment of the invention, the pulses are combined by a beam combiner. FIG. 7 is a diagram of an exemplary embodiment of a beam combiner according to an embodiment of the present invention. The three beams 902, 904 and 906 (selected for methane, an OFF-line signal and ethane) are each magnified by natural optical parametric amplifier (OPA) beam expansion, with a magnification of 3, and transmitted through optical couplers 920, 922 and 924. The beams are then transmitted through lenses 926, 928 and 930, respectively, and mask 908.

It has been determined by the inventor that a path length of approximately 250 mm from each OPA to each respective lens may be used. It has also been determined by the inventor that a diameter of approximately 7.0 mm for each lens 926, 928 and 930 may be used. It is contemplated that lenses having a different diameter and other path lengths may be used. It has also been determined by the inventor that a length of approximately 7.5 mm between the centers of each lens may be used.

Figure 7:
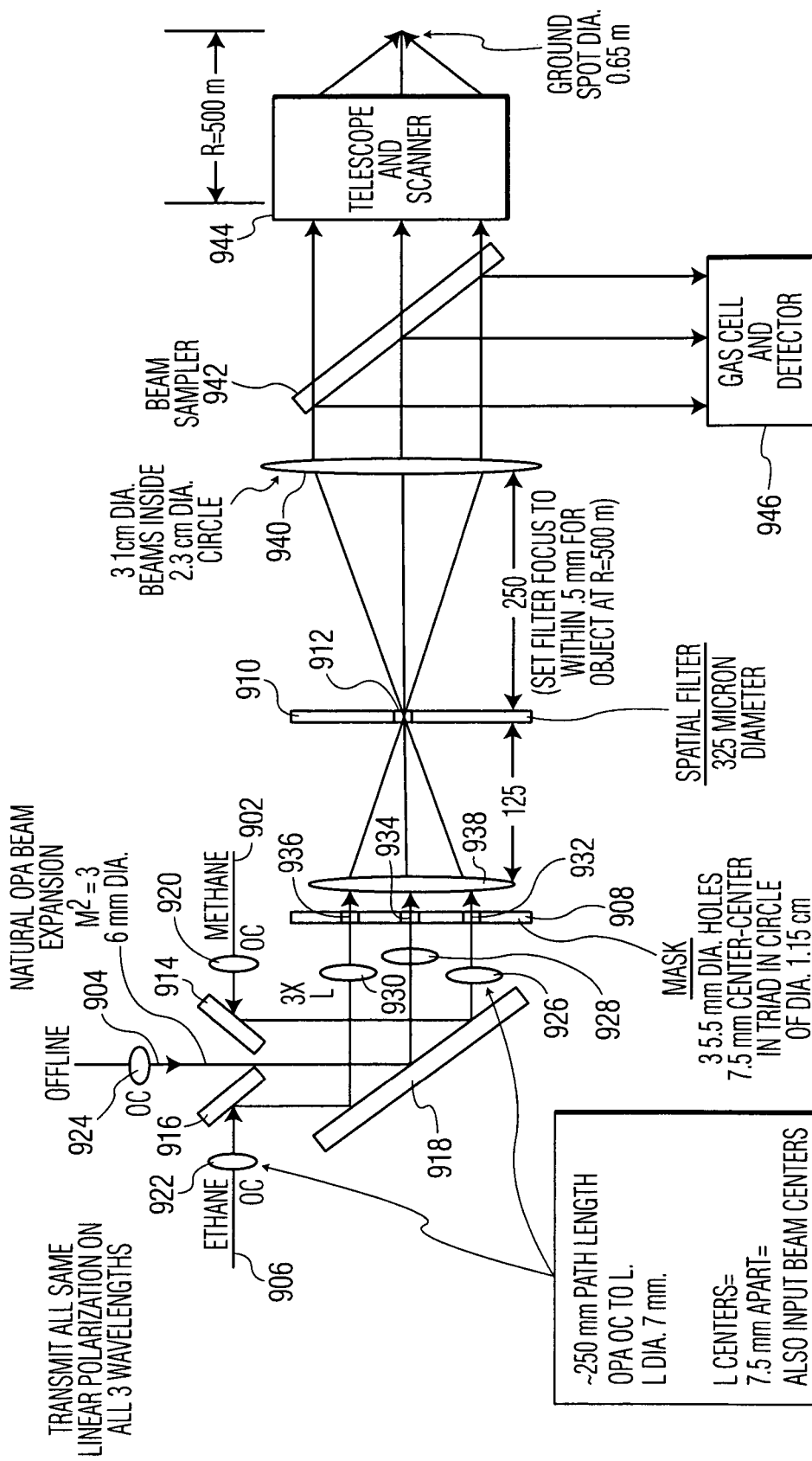
FIG. 7 is a schematic diagram illustrating a beam combiner, according to an embodiment of the present invention.

As also shown in FIG. 7, methane beam 902 and ethane beam 906 are redirected by reflectors 914 and 916, respectively, toward reflector 918. All three beams are redirected by reflector 918 through lenses 926, 928 and 930, and sent toward mask 908.

Figure 8A:
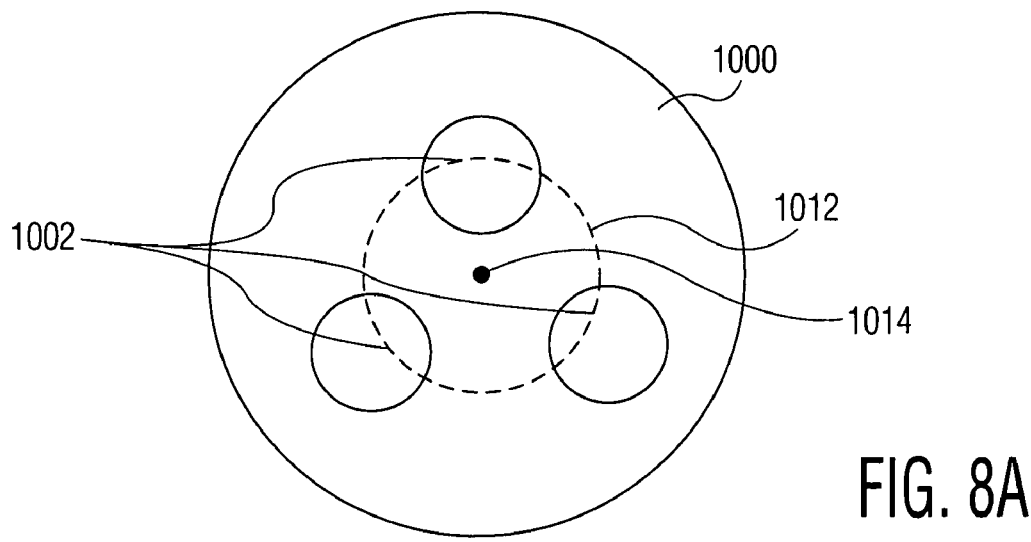
FIG. 8A is a front view of a mask used in the beam combiner of FIG. 7 to combine 3 beams, according to an embodiment of the present invention.

Mask 908 includes three apertures 932, 934 and 936, each having a diameter of about 5.5 mm, through which the beams may pass. It has been determined by the inventor that a length of approximately 7.5 mm between the centers of each aperture may be used. The apertures 932, 934 and 936, which are configured into a triangle within a circular area (908) having a diameter of about 1.15 cm, as illustrated in FIG. 8A.

Continuing the description of FIG. 7, beams 902, 904 and 906 are focused by lens 938 through focal aperture 912 of spatial filter 910. Spatial filter 910, which has a diameter of approximately 325 microns, affects the alignment of the three beams (902, 904 and 906) and generates a well defined extended beam overlap region. The inventor has determined that a filter focus to within approximately 0.5 mm may be used for a target at range of about 500 m. The common focal aperture 912 for the three beams (902, 904 and 906) and aperture mask 908 precisely define the beam overlap at the target range.

Misalignment between input beams 902, 904 and 906 due to, for example, pulse to pulse laser wander, bench thermal stresses, or setup alignment errors, may manifest as a loss of energy throughput for the misaligned beams, rather than a change in the distribution of the ground illumination. This effectively converts potential concentration length errors into benign transmitted pulse energy fluctuations. The energy fluctuations do not affect calibration and may be measured by pulse energy monitors.

Beams 902, 904 and 906, after passing through aperture 912, are transmitted to collimator lens 940, where they are aligned in parallel with respect to each other. The inventor has determined that a distance of about 125 mm between focus lens 938 and spatial filter 912 and a distance of about 250 mm between spatial filter 912 and lens 940 properly collimates the three beams. A portion of each beam 902, 904 and 906 is reflected by beam sampler 942 toward gas cell and detector 946. The remaining energy from each beam 902, 904 and 906 is sent to the ground by way of telescope and scanner assembly 944. From an altitude of about 500 m a spot on the ground is formed having a diameter of approximately 0.65 m.

Figure 8B:
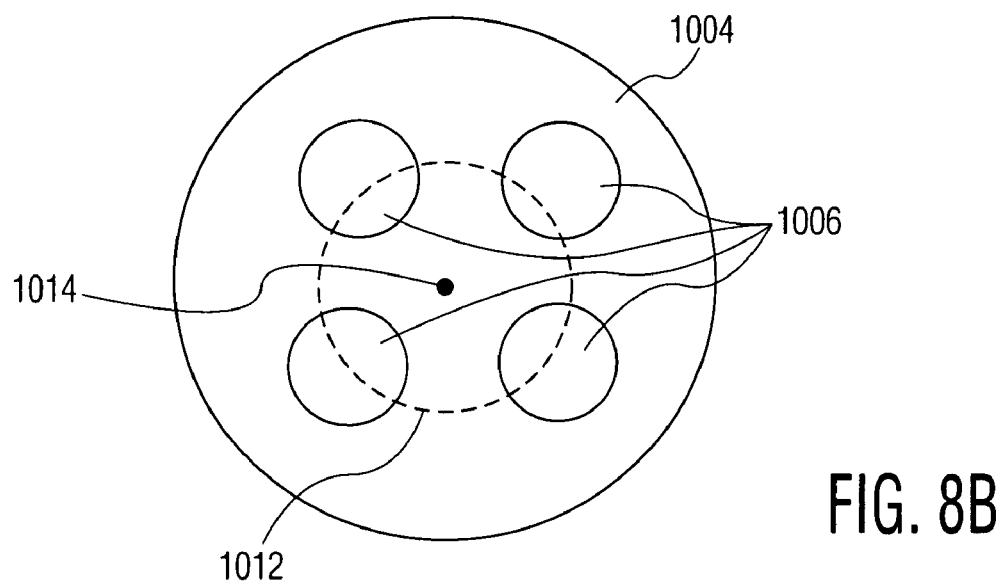
FIG. 8B is a front view of another mask for combining 4 beams, according to an embodiment of the present invention.
Figure 8C:
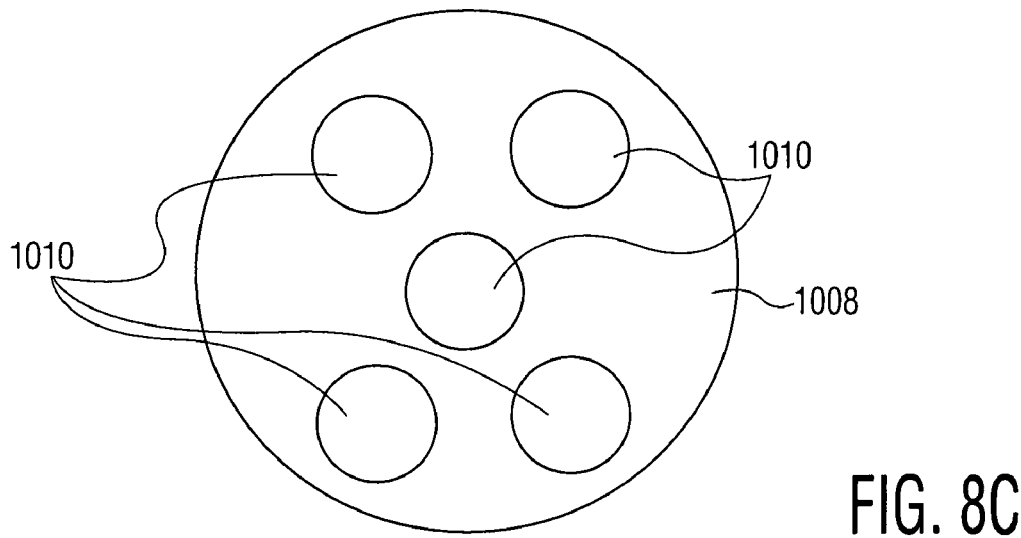
FIG. 8C is a front view of yet another mask for combining 5 beams, according to an embodiment of the present invention.

As described above, a 3-line laser system is used to exemplify the multi-line laser system. Accordingly, mask 908, shown in FIG. 7, includes three apertures 932, 934 and 936, as shown in FIG. 8A. Other exemplary masks may be used depending on the number of laser beams desired. FIGS. 8B and 8C are exemplary embodiments illustrating masks for combining four and five beams, respectively.

The mask shown in FIG. 8A combines 3 beams, as previously described. FIG. 8A shows 3 apertures 1002 in mask 1000. FIG. 8B shows 4 apertures 1006 in mask 1004 that may be used with a 4-line laser system. FIG. 8C shows 5 apertures 1010 in mask 1008 that may be used with a 5-line laser system. Although the masks shown in FIGS. 8A and 8B are arranged in a circle, it is contemplated that masks may be of other arrangements. Further, it is contemplated that the distance between the apertures may be different. For example, the apertures may be arranged on circle 1012 centered about axis 1014, as shown in FIGS. 8A and 8B.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A differential absorption light detection and ranging (DIAL) system comprising:
    a plurality of laser sources, each tunable to emit a beam of light;
    at least one tuning controller for real time tuning and locking of each beam of light to a predetermined wavelength having a spectral line-width, wherein each beam of light is tunable during real time operation of the DIAL system;
    a beam combiner for combining each beam of light to form a combined beam of light having multiple wavelengths;
    a transmitter for transmitting the combined beam of light toward the at least one target;
    a receiver for receiving light returning from the at least one target and converting returned light having multiple wavelengths to digital signals; and
    a processor for analyzing the digitized signals to identify the at least one target based on its multi-dimensional spectral characteristics;
    wherein the plurality of laser sources includes N lasers, N being an integer equal to or greater than 4,
    M of the lasers are each tuned to a wavelength that is partially absorbed by the target, M being an integer equal to or greater than 2,
    L of the lasers are tuned to a wavelength that is absorption-free of the target, L being an integer equal to or greater than 2,
    N is equal to M+L, and
    the N lasers are tuned to N different wavelengths for detecting the at least one target characterized by M different partially absorbed spectral lines, and L different spectral absorption-free lines; and
    the beam combiner comprising a mask, a focusing lens, a spatial filter and a collimator lens, arranged in spatial sequence,
    wherein the mask includes multiple apertures symmetrically arranged about a central point on the mask, each aperture configured to pass a respective beam of light at a predetermined wavelength,
    the focusing lens is configured to focus the beams of light transmitted from the multiple apertures,
    the spatial filter includes a central aperture, which is disposed symmetrically about the central point and is configured to transmit the beams of light toward the collimator lens, and
    the collimator lens is configured to receive diverging beams of light from the central aperture and combine the diverging beams of light into parallel beams of light.

2. A DIAL system according to claim 1, wherein the plurality of laser sources are each tunable to emit a beam of light in a mid-infrared spectrum.

3. A DIAL system according to claim 1, wherein at least one laser is tuned to a mid-infrared region of the spectrum and at least one other laser is tuned to a region outside of the mid-infrared region.

4. A DIAL system according to claim 1, wherein
    the plurality of laser sources are integrated into an airborne vehicle, and
    the at least one controller is configured for real time tuning and locking of each beam of light by an operator disposed in the airborne vehicle.

5. A DIAL system according to claim 4, wherein
    the at least one controller is configured for real time re-tuning and re-locking of each beam of light by the operator disposed in the airborne vehicle, after a first real time tuning and locking of each beam of light.

6. A DIAL system according to claim 1, wherein the plurality of laser sources are integrated into a vehicle, and the at least one controller is configured for real time tuning and locking of each beam of light by an operator disposed in the vehicle.

7. A DIAL system according to claim 6, wherein the at least one controller is configured for real time re-tuning and re-locking of each beam of light by the operator disposed in the vehicle, after a first real time tuning and locking of each beam of light.

8. The DIAL system of claim 7 further including a look-up-table (LUT) for selecting predetermined multi-dimensional spectral characteristics of different targets, and for tuning and re-tuning each beam of light to predetermined wavelengths corresponding to the selected multi-dimensional spectral characteristics.

9. A DIAL system according to claim 1, wherein the processor is configured to quantify at least one characteristic of the target based on the multi-dimensional spectral characteristics of the target.

10. A DIAL system according to claim 1, wherein each of the plurality of laser sources includes an optically pumped solid-state or semiconductor laser, a Q-switching device, seed lasers and an optical parametric oscillator (OPO) and optical parametric amplifier (OPA) for generating and tuning a respective beam of pulsed light at a respective predetermined wavelength, and the pulsed light is arranged to form a burst of pulses of a predetermined pulse width, pulse-to-pulse interval and pulse repetition interval.

11. A method for identifying multi-dimensional spectral characteristics of at least one target, the method comprising the steps of:

generating separate beams of light from a plurality of laser sources integrated in a DIAL system;

tuning and locking, in real time operation, each beam of light emitted from the plurality of laser sources to a predetermined wavelength having a spectral line-width;

combining each generated laser beam to form a combined beam of light having multiple wavelengths;

transmitting the combined beam of light having multiple wavelengths toward the at least one target;

receiving light returning from the at least one target; and converting the returned light to signals for identifying the at least one target based on spectral characteristics;

wherein the step of tuning and locking includes tuning and locking N lasers, N being an integer equal to or greater than 4, in which M of the lasers are each tuned to a wavelength that is partially absorbed by the target, M being an integer equal to or greater than 2.

L of the lasers are tuned to a wavelength that is absorption free of the target, L being an integer equal to or greater than 2, N is equal to M+L, and The N lasers are tuned to N different wavelengths for detecting the at least one target characterized by M different partially absorbed spectral lines, and L different spectral absorption free lines;

wherein the step of combining includes:

(a) passing the generated laser beams through multiple apertures that are symmetrically arranged about a central point on a mask, each aperture passing a respective beam at a predetermined wavelength, (b) focusing the beams passed through the multiple apertures onto a spatial filter having a central aperture disposed symmetrically about the central point, and (c) collimating the beams passed from the central aperture into parallel beams to form the combined beam of light.

12. A method according to claim 11, wherein the step of tuning and locking includes tuning and locking at least one laser to a mid-infrared region of the spectrum and at least one other laser to a region outside of the mid-infrared region.

13. A method according to claim 11, including integrating the plurality of laser sources into an airborne vehicle, and tuning and locking each beam of light, in real time, by an operator disposed in the airborne vehicle.

14. A method according to claim 13 including re-tuning and re-locking each beam of light, in real time, by the operator disposed in the airborne vehicle, after a first tuning and locking of each beam of light.

15. A method according to claim 11 including selecting from a look-up-table (LUT) predetermined multi-dimensional spectral characteristics of different targets, and tuning and re-tuning each beam of light to predetermined wavelengths corresponding to the selected multi-dimensional spectral characteristics.

16. The DIAL system of claim 1, wherein the combined beams of light are transmitted through a beam sampler for forming a spot on a ground target, and reflected from the beam sampler to a gas cell for providing a target reference.

17. The DIAL system of claim 1, wherein the combined beams of light are transmitted with the same polarization on each of the plurality of laser sources.

* * * * *